June 22, 1965 F. W. ANDERSON Plant Pat. 2,539
PLUM TREE
Filed March 5, 1964
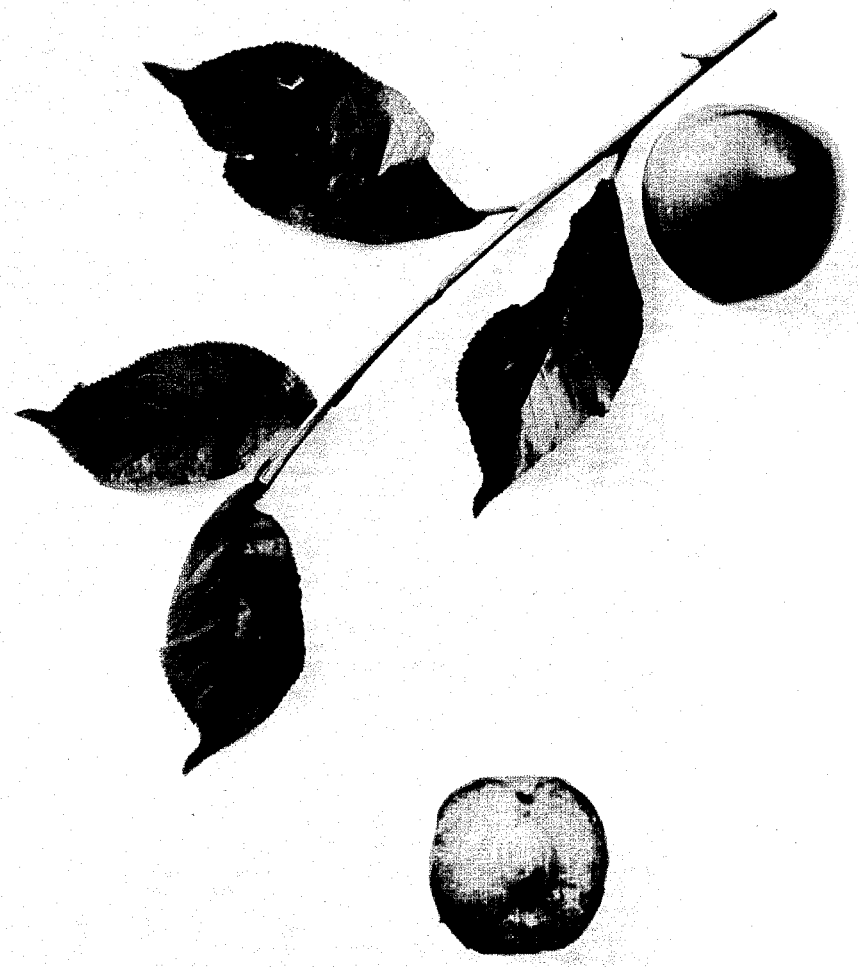
INVENTOR
*Frederic W. Anderson*
*Webster & Webster*
ATTYS.

United States Patent Office

Plant Pat. 2,539
Patented June 22, 1965

2,539
PLUM TREE

Frederic W. Anderson, Merced, Calif., assignor to Kim Bros., Reedley, Calif., a copartnership doing business under the fictitious name and style of Reedley Nursery Filed Mar. 5, 1964, Ser. No. 349,783
1 Claim. (Cl. Plt.—38)

This invention relates to a new and distinct variety of plum tree which is a regular and productive bearer of freestone fruit having a very early ripening period.

As compared to the Beauty (unpatented), which heretofore has been the earliest ripening commercial plum grown in and shipped from California, the fruit of the present variety is distinctively characterized by being in harvest approximately one week earlier than said Beauty.

In further comparison to the Beauty, the fruit of the present variety is slightly larger in size, has a brighter red exterior color, and is of superior eating quality.

The herein claimed variety of plum tree was originated by me as a cross between an unnamed early ripening seedling of the El Dorado and the Burmosa (all unpatented). Such origination of the variety was accomplished by me, in my experimental orchard located near Le Grand, Merced County, California, during the course of a long and continuing program seeking improved fruit varieties, including plums.

Subsequent to origination of the variety and the recognition by me of its novel and desirable characteristics, I asexually reproduced it by top-working on mature trees in my experimental orchard located as aforesaid. Such asexual reproductions ran true to the parent tree in all respects.

The drawing is an illustration, by photographic reproduction in color, of a twig with leaves; a whole fruit; and one half of a fruit cut to expose the flesh and with the stone remaining in place.

Referring now more specifically to the pomological details of this new and distinct variety of plum tree, the following is an outline description thereof; all major color plate identifications being by reference to Maerz and Paul Dictionary of Color, except where common terms of color definition are employed.

Tree:
- *Size.*—Medium.
- *Vigor.*—Vigorous.
- *Growth.*—Spreading.
- *Production.*—Productive.
- *Bearing.*—Regular bearer.

Trunk: Form—medium.

Branches:
- *Form.*—Medium.
- *Texture.*—Medium.
- *Color.*—On current season's growth, red on side exposed to the sun.

Leaves:
- *Size.*—Large to medium. Average length 3½". Average width—1¾".
- *Form.*—Obovate; acutely pointed.
- *Thickness.*—Medium.
- *Texture.*—Smooth.
- *Margin.*—Crenate.
- *Petiole.*—Medium length; medium thickness.
- *Glands.*—Average number—4. Usually positioned 2 on petiole and 2 or more on blade. Opposite; medium size; globose; red.
- *Color.*—Top side—medium green (22–L–9). Under side—lighter green (22–H–6).

Flower buds:
- *Length.*—Short.
- *Form.*—Obtuse.

Flowers:
- *Blooming period.*—Date of first bloom—March 1, 1963. Date of full bloom—March 6, 1963. Medium, as compared with other oriental type plums.
- *Color.*—White.

Fruit:
- *Maturity when described.*—Eating ripe—June 10, 1963.
- *Date of first picking.*—June 5, 1963.
- *Date of last picking.*—June 14, 1963.
- *Size.*—Uniform to variable; medium. Average diameter axially—2". Average transversely in suture plane—1⅞".
- *Form.*—Uniform; globose.
- *Suture.*—Shallow.
- *Cavity.*—Rounded. Average depth—⅝". Average breadth—9/16".
- *Base.*—Rounded.
- *Apex.*—Short.

Skin:
- *Thickness.*—Medium.
- *Texture.*—Medium.
- *Tendency to crack.*—None.
- *Down.*—Wanting.
- *Color.*—Brighter red than Beauty when picking ripe, shading to reddish purple (47–L–8) when full ripe.

Flesh:
- *Texture.*—Medium; crisp; melting.
- *Fibers.*—Few; tender.
- *Ripens.*—Evenly.
- *Flavor.*—Subacid; delicate.
- *Eating quality.*—Good.
- *Color.*—Yellow (11–L–5) when picking ripe, but by gradual change a deeper dark red, as illustrated, when full ripe.

Stone:
- *Type.*—Free.
- *Size.*—Medium to small. Average length—¾". Average breadth—⅝". Average thickness—¼".
- *Color*—Beige (13–L–8).

Use: Market.

Keeping quality: Medium.

Shipping quality: Medium.

The plum tree and its fruit herein described may vary in slight detail due to climatic and soil conditions under which the variety may be grown; the present description being of the variety as grown in the Central Valley of California.

The following is claimed:

A new and distinct variety of plum tree, as illustrated and described, which is a regular and productive bearer of medium size, early ripening, freestone fruit; characterized, in comparison to the Beauty, by fruit which ripens approximately one week earlier, is of slightly larger size, has a brighter red exterior color, and is of superior eating quality.

No references cited.

ABRAHAM G. STONE, *Primary Examiner.*